US009000209B2

(12) United States Patent
Kraus

(10) Patent No.: US 9,000,209 B2
(45) Date of Patent: Apr. 7, 2015

(54) METHOD OF REGIOSELECTIVE SYNTHESIS OF SUBSTITUTED BENZOATES

(75) Inventor: George A. Kraus, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

(21) Appl. No.: 14/234,079

(22) PCT Filed: Jun. 21, 2012

(86) PCT No.: PCT/US2012/043580
§ 371 (c)(1),
(2), (4) Date: May 20, 2014

(87) PCT Pub. No.: WO2013/015918
PCT Pub. Date: Jan. 31, 2013

(65) Prior Publication Data
US 2014/0288324 A1    Sep. 25, 2014

Related U.S. Application Data

(60) Provisional application No. 61/510,661, filed on Jul. 22, 2011.

(51) Int. Cl.
C07C 67/313    (2006.01)
C07C 51/377    (2006.01)
C07C 67/317    (2006.01)
C07C 67/343    (2006.01)
C07C 51/367    (2006.01)

(52) U.S. Cl.
CPC ............. *C07C 67/317* (2013.01); *C07C 67/313* (2013.01); *C07C 67/343* (2013.01); *C07C 51/367* (2013.01); *C07C 51/377* (2013.01); *C07C 2103/66* (2013.01); *C07C 2103/86* (2013.01)

(58) Field of Classification Search
USPC ............ 560/64, 102, 103; 562/473, 492, 493
See application file for complete search history.

(56) References Cited

U.S. PATENT DOCUMENTS 7,385,081 B1    6/2008  Gong

FOREIGN PATENT DOCUMENTS

WO    WO-2009064515 A1    5/2009
WO    WO-2009105500 A1    8/2009
WO    WO-2013015918 A1    1/2013

OTHER PUBLICATIONS

"International Application Serial No. PCT/US2012/043580, Search Report mailed Sep. 13, 2012", 4 pgs.
"International Application Serial No. PCT/US2012/043580, Written Opinion mailed Sep. 13, 2012", 3 pgs.
Kraus, George A, et al., "Aromatics from Pyrones", Para-Substituted Alkyl Benzoates from Alkenes, Coumalic Acid and Methyl Coumalate. vol. 13. Green Chemistry, Downloaded at http://pubs.rsc.org/En/content/articlelanding/2011/gc/c1gc15650k. Abstract only, (Aug. 22, 2011), 2734-2736.
Matsushita, Yoh-Ichi, et al., "A Convenient Synthesis of Methyl 4-Substituted Benzoates Via Diels-Alder Reaction in the Presence of Palladiumb on Activated Carbon", Synthetic Communications, (1994), 3307-3313.
Pratt, Andrew J, et al., "Thermal Decomposition of 1, 1-bis(methylthio)ethene, Pyran-2-one Diels-Alder Adducts", An Unusual [1,5]-Sulfenyl Rearrangement. Arkivoc, [online] URL=<http://www.arkat-usa.org/get-file/19778/>, (2006), 211-212.
"International Application Serial No. PCT/US2012/043580, International Preliminary Report on Patentability mailed Feb. 6, 2014", 5 pgs.
Afarinkia, K., et al., "Diels-Alder cycloadditions of 2-pyrones and 2-pyridones", Tetrahedron, 48(42), (1992), 9111-9171.
Amatore, Muriel, et al., "Synthesis of functionalised diarylmethanes via a cobalt-catalysed cross-coupling of arylzinc species with benzyl chlorides", Chem. Commun., 40, (2008), 5019-5021.
Ashworth, I. W, et al., "A New Route for Manufacture of 3-Cyano-1-naphthalenecarboxylic Acid", Org. Proc. Res. Dev., 7(1), (2003), 74-81.
Bryson, T. A, et al., "Diels-Alder synthesis of hindered aromatic amines", J. Org. Chem., 42(17), (1977), 2930-2931.
Delaney, P. M, et al., "A 2-pyrone cycloaddition route to functionalised aromatic boronic esters", Tetrahedron, 64(5), (Jan. 28, 2008), 866-873.
Kraus, George A, "Chapter 10: Phytochemicals, Dyes, and Pigments in the Biorefinery Context", Biorefineries-Industrial Processes and Products, Wiley-VCH Verlag GmbH, (2006), 315-324.
Kraus, George A, "Synthetic Methods for the Preparation of 1,3-Propanediol", CLEAN—Soil, Air, Water, 36(8), (Aug. 2008), 648-651.
Leijondahl, Karin, et al., "Enantiopure 1,5-Diols from Dynamic Kinetic Asymmetric Transformation. Useful Synthetic Intermediates for the Preparation of Chiral Heterocycles", Org. Lett.,10(10), (2008), 2027-2030.
Savard, Jacques, et al., "Reactions of ketene acetals-14 The use of simple mixed vinylketene acetals in the annulation of quinones", Tetrahedron, 40(18), (1984), 3455-3464.
Sheehan, Richard J, "Terephthalic Acid, Dimethyl Terephthalate, and Isophthalic Acid", Ullmann's Encyclopedia of Industrial Chemistry, (Jun. 15, 2000), 21 pgs.
Zeitsch, Karl J, "Chapter 16. Diacetyl and 2,3-Pentanedione", The Chemistry and Technology of Furfural and its Many By-Products, Amsterdam ; New York : Elsevier, (2000), 137.

*Primary Examiner* — Sikarl Witherspoon
(74) *Attorney, Agent, or Firm* — Schwegman Lundberg & Woessner, P.A.

(57) ABSTRACT

A method of synthesis of para-substituted benzoate esters and acids is provided, wherein the para-substituted regioisomer is obtained substantially free of the meta-substituted impurity, the method comprising contacting a coumalate ester or acid and an unactivated alkene at elevated temperature in the presence of a metal oxidation catalyst and an oxidant. The metal oxidation catalyst can be palladium, such as palladium on carbon, and the oxidant can be the oxygen gas in ambient air. The reaction can be carried out without solvent or in high boiling hydrocarbon solvents such as mesitylene. When the unactivated alkene is a monosubstituted alkene, yields of at least about 50 or 60% of para-substituted ester and acid products, respectively, are obtained, substantially free of the regioisomeric meta-substituted impurity.

20 Claims, No Drawings

METHOD OF REGIOSELECTIVE SYNTHESIS OF SUBSTITUTED BENZOATES

This application is a U.S. National Stage Application under 35 U.S.C. §371 of International Application No. PCT/US2012/043580, filed Jun. 21, 2012, which application claims priority to U.S. Provisional Application Ser. No. 61/510,661, filed Jul. 22, 2011, which applications are incorporated herein by reference in their entirety.

STATEMENT OF GOVERNMENT SUPPORT

This invention was made with Government support under grant number EEC0813570, awarded by the National Science Foundation. The U.S. Government has certain rights in the invention.

BACKGROUND

The development of new, cost-competitive processes that utilize renewable resources as feedstocks is vital for a sustainable economy. These processes also represent important milestones toward the goal of reducing the United States' dependence on foreign oil. Introduction of such processes not only avoids the use of more petroleum, but also has the potential to provide substantial energy savings, and reduce greenhouse gas emissions. Although biobased syntheses of certain commercially significant compounds such as 1,3-propanediol have been reported,[1] there are comparatively few reported approaches[2] to compounds related to terephthalic acid.

The Diels-Alder reaction of pyrones such as coumalic esters with activated alkynes has good literature precedent.[3,4] As shown in Scheme 1, the reaction with methyl coumalate (1) involves a cycloaddition to produce bicyclo[2.2.2]octadiene intermediate 2 that loses carbon dioxide to directly form the substituted benzene. Delaney, et al., have utilized this reaction to produce phenols.[5] The reaction of activated alkenes, such as acrylates or acrylonitrile, with methyl coumalate can produce a bicyclic lactone 3 that cannot go directly to an aromatic ring by loss of carbon dioxide. One way to construct aromatic rings via this intermediate is to dehydrogenate adduct 3 under conditions that lead to loss of carbon dioxide.[6]

Scheme 1: Diels-Alder reaction with activated alkenes

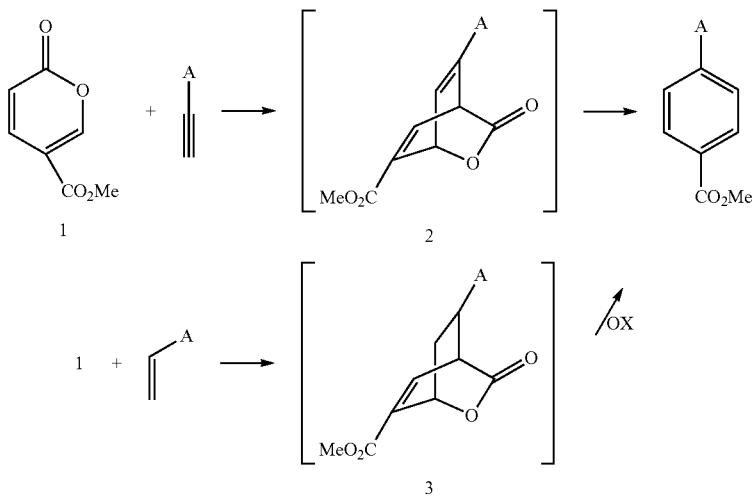

However, a need exists for methods to condense coumalates with unactivated (electron-rich) alkenes.

SUMMARY

The invention is directed, in various embodiments, to a method of synthesis of a para-substituted benzoate, comprising contacting a coumalate compound of formula (I)

an alkene of formula $CH_2=CHR^1$, a metal oxidation catalyst, and an oxidant, under conditions so as to provide the para-substituted benzoate of formula

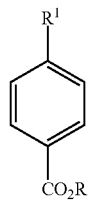

wherein R is H, alkyl, aryl, arylalkyl, cycloalkyl, or cycloalkylalkyl, and $R^1$ is alkyl, alkoxyalkyl, arylalkyl, aryloxyalkyl, or arylalkoxyalkyl. Groups termed $R^1$ as defined herein are electron-releasing groups, resulting in an alkene $CH^2=CHR^1$ that would not be termed as an activated alkene with respect to reaction as a dienophile in a Diels-Alder cycloaddition reaction.

In various embodiments, the product resulting from contacting the coumalate compound of formula (I) and the alkene is substantially free of a regiomeric meta-substituted benzoate impurity of formula

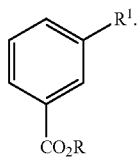

In various embodiments, the invention provides a method further comprising conversion of the para-substituted benzoate to a terephthalate by oxidation of group $R^1$, to provide a terephthalate substantially free of impurity isophthalate.

In various embodiments, the invention provides a method further comprising conversion of the terephthalate to a polyester polymer by condensation of the terephthalate with a diol, to provide a telephthalate polymer substantially free of isophthalate moieties.

In various embodiments, the invention provides a method of synthesis of a substituted benzoate, comprising contacting a coumalate compound of formula (I)

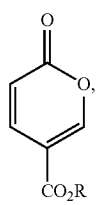

an alkene of formula $R^1CH=CHR^2$, a metal oxidation catalyst, and an oxidant, under conditions suitable to provide the substituted benzoate of formula

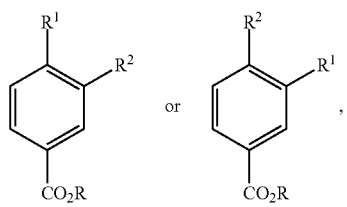

or a mixture thereof;

wherein R is H, alkyl, aryl, arylalkyl, cycloalkyl, or cycloalkylalkyl, and $R^1$ and $R^2$ are independently alkyl, alkoxyalkyl, arylalkyl, aryloxyalkyl, or arylalkoxyalkyl, or wherein $R^1$ and $R^2$ together with the atoms to which they are bonded form a cycloalkene ring of more than about six members; wherein any alkyl, alkoxyalkyl, arylalkyl, aryloxyalkyl, or arylalkoxyalkyl, or cycloalkene, of $R^1$ and $R^2$ can be substituted with alkyl, hydroxy, alkoxy, or carboxalkyl groups.

In various embodiments, the invention provides a method of synthesis of a linker-bonded benzoate dimer of formula

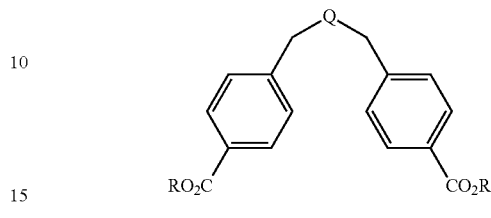

wherein both R groups are H, alkyl, aryl, arylalkyl, cycloalkyl, or cycloalkylalkyl, and Q is an alkylene group of at least one carbon; comprising contacting a coumalate compound of formula (I)

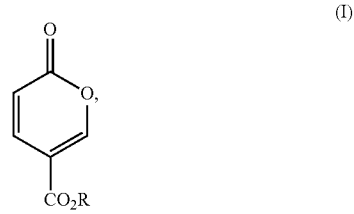

an alkene of formula $CH_2=CHCH_2QCH_2CH=CH_2$, a metal oxidation catalyst, and an oxidant, under conditions suitable to provide the substituted linker-bonded benzoate dimer.

In contrast to the results with unactivated alpha-olefins, the reaction of either methyl coumalate or coumalic acid with the activated olefin, methyl acrylate, provided a 1:1 mixture of meta- and para-substituted products. A further embodiment of the invention provides a method for the selective synthesis of the meta-substituted compound (II), free from the para-product, wherein R is as defined above. When R is methyl, compound II is methyl(3-carboxybenzoate) or monomethylisophthlate, that is free from the 4-carboxybenzoate. Hydrolysis of the mono methyl ester yields isophthalic acid in one step.

Isophthalic acid is a useful intermediate in the preparation of commercially important polymers, such as polybenzimidazoles[10].

A sterically demanding salt of acrylic acid is synthesized by combining equimolar quantities of acrylic acid and a sterically hindered amine, e.g., a tertiary trialkyl amine such as diisopropyl(ethyl)amine, as in Scheme 2(b). This salt could be prepared in situ and treated with methyl coumalate using the general reaction condition as described above. These include contacting (I) with the formylate salt (IV) at about 125-175° C. in the presence of a Pd catalyst, e.g., Pd/C in the present of $O_2$, preferably in the absence of solvent. Surprisingly, as shown in Scheme 2(a), the reaction yielded only the meta-product (II).

Scheme 2

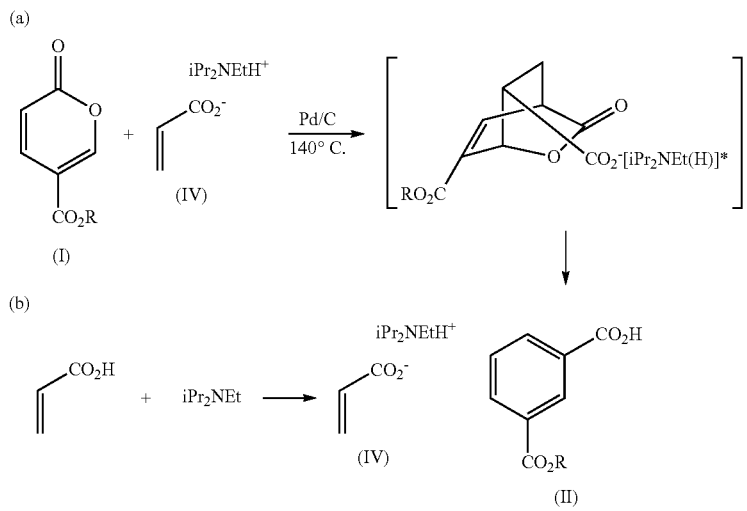

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

Alkyl groups include straight chain and branched alkyl groups and cycloalkyl groups having from 1 to about 20 carbon atoms, and typically from to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-, 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "unactivated alkene" as used herein refers to an compound comprising an alkenyl group wherein the alkenyl double bond is not substituted with an electron withdrawing group, such as can activate a double (or triple) bond as a dienophile to react with a diene in a Diels-Alder cycloaddition reaction. Accordingly, an alkene of formula $CH_2=CHR^1$ as described herein does not include compounds wherein $R^1$ is an electron withdrawing group such as a nitrile group, a carboxylate group, or other electron deficient groups such as are well-known in the art, which would be referred to as "activated alkenes", i.e., activated as Diels-Alder dienophiles. As is well known in the art, a normal Diels-Alder reaction involves an electron-rich diene and an electron-deficient ("activated") dienophile. In the presented disclosed method, the dienophile is not "activated" in the sense that it does not bear an electron-withdrawing group, which ordinary knowledge would suggest to be unreactive in a Diels-Alder cycloaddition reaction. Rather, the alkene dienophile is an alkene bearing electron-donating groups such as alkyl or alkoxy.

An unactivated alkene of the formula $R^1CH=CHR^2$ as defined herein includes a linear, branched, or cyclic alkene, wherein $R^1$ and $R^2$ do not comprise activating (i.e., as a Diels-Alder dienophile) groups conjugated with the double bond. Accordingly, $R^1$ and $R^2$ can be alkyl, alkylaryl, alkoxyalkyl, cycloalkyl, cycloalkylalkyl or other electron-donating groups such as are well known in the art. The double bond can be of the (Z) or the (E) configuration, i.e., of the cis or trans configuration for the alkene of formula $R^1CH=CHR^2$. A cycloalkene of suitable size to incorporate a trans double bond can be used, although most cycloalkenes of ring size of about eight or less are most stable in their cis forms.

A diene such as can be used in a method disclosed herein for preparation of a linker-bonded benzoate dimer includes α,ω-dienes of at least about seven carbon atoms, e.g., 1,6-heptadiene, 1,7-octadiene, 1,8-nonadiene, and the like.

A linker-bonded benzoate dimer, as the term is used herein, refers to a molecule of formula

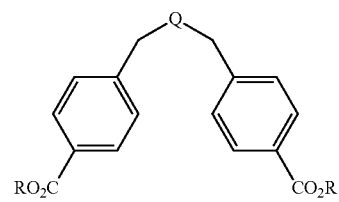

wherein both R groups are H, alkyl, aryl, arylalkyl, cycloalkyl, or cycloalkylalkyl, and, Q is an alkylene group of at least one carbon atom, e.g., having 1-4 carbon atoms.

The term "ambient air", as used herein, refers to a reaction carried out exposed to the atmosphere.

An "oxidation catalyst", such as a "metal oxidation catalyst", refers to a material that can be present in less than stoichiometric quantities that brings about a reaction between an oxidant, such as oxygen gas, and a reactant, at a lower temperature and/or a higher rate than is achieved under comparable conditions without the presence of the material.

The reaction of methyl coumalate and coumalic acid with unactivated terminal alkenes was studied. It is believed that such terminal alkenes have not previously been reported to react with coumalic acid. Matsushita and coworkers have reported the reactions of substituted styrenes with pyrones.[6] In order to generate the requisite bicyclo[2.2.2]octadiene intermediate, the Diels-Alder reaction was conducted in the presence of catalytic amounts of 10% Pd/C. Because unactivated alkenes are employed in the Diels-Alder reaction, both 4 and 5 could theoretically be produced (see Scheme 3).

Scheme 3: Possible regiomeric outcomes from Diels-Alder Reaction of methyl coumalate with unactivated alkenes

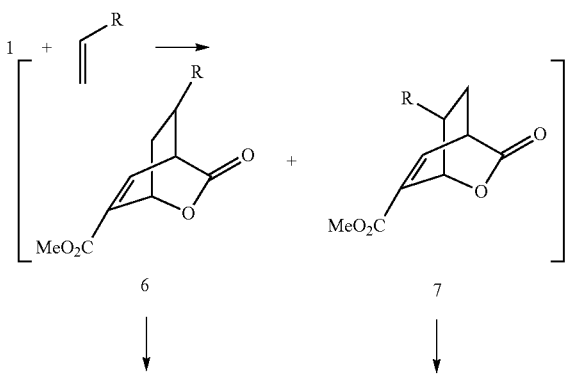

-continued

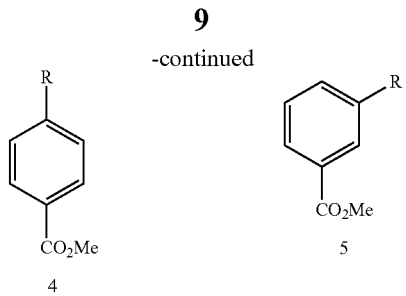

4

5

As the results in Table 1 indicate, only the para-substituted adduct 4 was produced, as evidenced by the proton NMR and, in the case of entry 4, by comparison with an authentic sample.[7] Interestingly, aromatic ethers and aliphatic ethers are compatible with the reaction conditions.

TABLE 1

The reaction of methyl coumalate with alkenes

| Entry | Substrate | Yield | R Group | Product |
|---|---|---|---|---|
| 1 | 1-nonene | 52% | —$(CH_2)_6CH_3$ | 4a |
| 2 | 1-decene | 70% | —$(CH_2)_7CH_3$ | 4b |
| 3 | 1-undecene | 63% | —$(CH_2)_8CH_3$ | 4c |
| 4 | allyl benzene | 83% | —$CH_2Ph$ | 4d |
| 5 | allyl phenyl ether | 61% | —$CH_2OPh$ | 4e |
| 6 | allyl heptyl ether | 51% | —$CH_2O(CH_2)_6CH_3$ | 4f |

The Diels-Alder reactions were also examined using coumalic acid. Although it was less soluble than methyl coumalate at ambient temperature, the reaction became homogeneous around 140° C. The results are shown below in Table 2.

TABLE 2

The reaction of coumalic acid with alkenes

| Entry | Substrate | Yield | R Group | Product |
|---|---|---|---|---|
| 1 | 1-heptene | 85% | —$(CH_2)_6CH_3$ | 8a |
| 2 | 1-decene | 72% | —$(CH_2)_7CH_3$ | 8b |
| 3 | 1-undecene | 69% | —$(CH_2)_8CH_3$ | 8c |
| 4 | allyl benzene | 79% | —$CH_2Ph$ | 8d |
| 5 | allyl phenyl ether | 65% | —$CH_2OPh$ | 8e |
| 6 | allyl heptyl ether | 66% | —$CH_2O(CH_2)_6CH_3$ | 8f |

The rationale for the remarkable regioselectivity is unclear. Although the result may simply be due to non-bonded steric interactions, the selective oxidation by Pd/C of 6 (the adduct that would lead to the para-substituted product) over 7 (the adduct that would lead to the meta-substituted product) may occur.

The invention is directed in various embodiments to a method of synthesis of a para-substituted benzoate, comprising contacting a coumalate compound of formula (I)

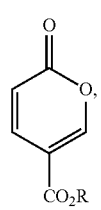

(I)

an alkene of formula $CH_2$=$CHR^1$, a metal oxidation catalyst, and an oxidant, are under conditions suitable to provide the para-substituted benzoate of formula

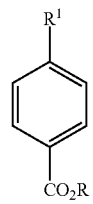

5 wherein R is H, alkyl, aryl, arylalkyl, cycloalkyl, or cycloalkylalkyl, and
$R^1$ is alkyl, alkoxyalkyl, arylalkyl, aryloxyalkyl, or arylalkoxyalkyl.

For example, R can be alkyl. More specifically, R can be methyl. Methyl coumalate is readily prepared from coumalic acid, a known compound.

In other embodiments, R is H. Coumalic acid in free form has been found to undergo the same regioselective Diels-Alder cycloaddition with subsequent oxidation to selectively provide the para-benzoate product, i.e., the para-substituted benzoic acid when coumalic acid is used as the starting material.

In various embodiments, the unactivated alkene that can undergo the reaction with coumalates as described herein can be a compound of formula $CH_2$=$CHR^1$ wherein $R^1$ is alkyl. An unactivated alkene would not be expected by a person of ordinary skill in the art to undergo a Diels-Alder cycloaddition reaction, as typically a Diels-Alder reaction involves condensation of a diene with an unsaturated compound that is electron-deficient, e.g., an acrylate or acrylonitrile, wherein the alkenyl double bond bears an electron-withdrawing group such as a carboxylate or nitrile group.

As shown in Scheme 3, above, the reaction is believed to proceed via a bicyclic intermediate, compound 6, which undergoes elimination of $CO_2$, and dehydrogenation, to provide the fully aromatic product 4. The elimination of $CO_2$ is believed to proceed thermally, but the dehydrogenation step requires an oxidation, which is accomplished in the presence of the metal oxidation catalyst and the oxidant.

In various embodiments, the metal oxidation catalyst comprises palladium. The palladium is conveniently provided in the reaction mixtures as palladium on carbon, such as commercially available 5% or 10% palladium on carbon.

The oxidant and the intermediate undergoing dehydrogenation, postulated as compound 6, react in the presence of the metal oxidation catalyst, e.g., palladium. The oxidant can be any suitable oxidant that yields the benzoate from the dihydrobenzoate produced from decarboxylation of 6, but oxygen, such as is present in ambient air, is readily available and is suitable for the dehydrogenation reaction. The dehydrogenation and decarboxylation steps occur spontaneously under the reaction conditions, and intermediate 6 or its decarboxylation product are not isolated.

In various embodiments, the reaction conditions can comprise contacting the coumalate compound of formula (I) and the alkene at an elevated temperature, optionally in a solvent. For example, the elevated temperature can be about 140° C. to 200° C. Although the reaction can be carried out in a neat melt, the contacting can also be carried out in a solvent, such as a hydrocarbon or an ether, or both, of a boiling point of not less than about 190° C. For example, the solvent can comprise mesitylene, a high boiling aromatic hydrocarbon. When coumalic acid is used, solubility in mesitylene is not as great as is the solubility of methyl coumalate, but the acid goes into solution in mesitylene at effective concentrations at temperatures of about 140° C. or higher.

An outstanding advantage of the present method is that the product resulting from contacting the coumalate compound of formula (I) and the unactivated alkene is substantially free of a regiomeric meta-substituted benzoate impurity 5 of formula

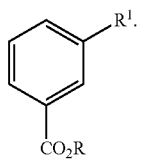

As shown in Scheme 3, above, two theoretical intermediates, 6 and 7, can be envisioned, yet only the para-substituted product 4 and not the meta-substituted 5 is detected in significant quantities in the reaction product. For example, when R is H, a yield of the para-substituted benzoic acid is at least about 60% and can range up to more than about 80%. When a coumalate ester is used, such as methyl coumalate, the yield of the para-substituted benzoate can be at least about 50%, and can also range upwards to greater than about 80%.

The reaction product can be readily purified by cooling the reaction vessel to room temperature, then removing the catalyst by filtering through a pad of Celite, then washing with ether. The filtrate can then be concentrated and purified by silica gel column chromatography (e.g., in 10:1 hexanes/ethyl acetate as elution solvent).

In various embodiments, the invention provides a method further comprising conversion of the para-substituted benzoate obtained by the above-described method to a terephthalate by oxidation of group R, as is well known in the art. See, for example, Richard J. Sheehan, "Terephthalic Acid, Dimethyl Terephthalate, and Isophthalic Acid" in Ullmann's Encyclopedia of Industrial Chemistry, Wiley-VCH, Weinheim, 2002. doi:10.1002/14356007.a26_193 Article Online Posting Date: Jun. 15, 2000. Due to the high regioselectivity for production of the para-substituted product by the inventive process, the terephthalate is substantially free of an isophthalate meta-substituted impurity. See also: Nakai, Takeo; Iwai, Toshiyuki; Mihara, Masatoshi; Ito, Takatoshi; Mizuno, Takumi, *Tetrahedron Letters* (2010), 51(17), 2225-2227. DOI: 10.1016/j.tetlet.2010.02.069; Paul, Satya; Nanda, Puja; Gupta, Rajive, *Synlett* (2004), (3), 531-533. DOI: 10.1055/s-2004-815418; Hirai, Naruhisa; Sawatari, Naoko; Nakamura, Norihiro; Sakaguchi, Satoshi; Ishii, Yasutaka, *Journal of Organic Chemistry* (2003), 68(17), 6587-6590. DOI: 10.1021/jo034313z.

In various embodiments, a method of the invention further comprises conversion of the terephthalate to a polyester polymer by condensation of the terephthalate with a diol. For example, condensation of the terephthalate with ethylene glycol can be used to produce polyethyleneterephthalate or condensation of the terephthalate with butylene glycol can be used to produce polybutyleneterephthalate. Again, due to the high regioselectivity for production of the para-substituted by the inventive process, the terephthalate-containing polymer is substantially free of isophthalate moieties.

Further studies were carried out to investigate the scope of the reaction with respect to reactive olefins. Table 3 shows that the reaction proceeds when using disubstituted alkenes with electron donating groups and cyclic alkenes, as indicated, but generally does not proceed when the olefin is an unactivated alkene, as the term unactivated is defined herein, i.e., unactivated as a dienophile in a typical Diels Alder reaction. An alkene is activated as a Diels Alder dienophile when it bears electron withdrawing groups, such as a carboxylate group.

TABLE 3

Reactions of methyl coumalate and coumalic acid with various substrates

| Entry | Pyrone | Substrate | Scale | Conversion |
|---|---|---|---|---|
| 1 | methyl coumalate | propiolic acid | 450 mg | trace (complex mixture) |
| 2 | methyl coumalate | propargyl alchol | 450 mg | trace |
| 3 | methyl coumalate | 4-vinyl cyclohexene | 200 mg | NR |
| 4 | methyl coumalate | diallyl ether | 200 mg | NR |
| 5 | methyl coumalate | allyl benzyl ether | 200 mg | NR (complex mixture) |
| 6 | methyl coumalate | allyl phenyl ether | 200 mg | 61% |
| 7 | methyl coumalate | allyl benzene | 200 mg | 83% |
| 8 | methyl coumalate | 1-nonene | 200 mg | 52% |
| 9 | methyl coumalate | 1-decene | 200 mg | 70% |
| 10 | methyl coumalate | 1-undecene | 200 mg | 63% |
| 11 | methyl coumalate | allyl heptyl ether | 200 mg | 51% |
| 12 | methyl coumalate | trans-y-4-octene | 200 mg | 45% |
| 13 | methyl coumalate | cis-cyclodecene | 200 mg | 70% |
| 14 | methyl coumalate | cis-cyclooctene | 200 mg | 62% |
| 15 | methyl coumalate | cis, trans-cyclododecene | 200 mg | 70% |
| 16 | methyl coumalate | allyl acetate | 200 mg | NR |
| 17 | methyl coumalate | allyl benzoate | 200 mg | NR |
| 18 | methyl coumalate | t-butyl acrylate | 200 mg | trace (meta product dominates) |
| 19 | coumalic acid | 1-heptene | 200 mg | 85% |
| 20 | coumalic acid | 1-decene | 200 mg | 67% |
| 21 | coumalic acid | 1-decene | 500 mg | 72% |
| 22 | coumalic acid | 1-decene | 1 g | 60% |
| 23 | coumalic acid | 1-undecene | 200 mg | 69% |
| 24 | coumalic acid | allyl benzene | 200 mg | 79% |
| 25 | coumalic acid | allyl phenyl ether | 200 mg | 65% |
| 26 | coumalic acid | allyl heptyl ether | 200 mg | 66% |
| 27 | coumalic acid | methyl dec-9-enoate | 200 mg | 78% |
| 28 | methyl coumalate | 1,5-hexadiene | 200 mg | NR |
| 29 | methyl coumalate | 4-pentenoic acid | 200 mg | NR |
| 30 | methyl coumalate | 1,7-octadiene | 200 mg | 60% |
| 31 | coumalic acid | 1,9-decadiene | 500 mg | 49% |
| 32 | coumalic acid | 1,8-nonadiene | 500 mg | 65% |
| 33 | coumalic acid | norbornene | 500 mg | 83% |
| 34 | coumalic acid | norbornadiene | 500 mg | 71% |
| 35 | coumalic acid | methyl oleate | 500 mg | 23% (isolated yield, difficult to separate) |
| 36 | methyl coumalate | maleic anhydride | 220 mg | 77% |
| 37 | coumalic acid | diallyl benzene | 400 mg | 53% |

In various embodiments, the invention provides a method of synthesis of a substituted benzoate, comprising contacting a coumalate compound of formula (I)

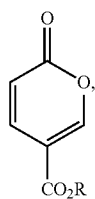

an alkene of formula $R^1CH$=$CHR^2$, a metal oxidation catalyst, and an oxidant, under conditions suitable to provide the substituted benzoate of formula

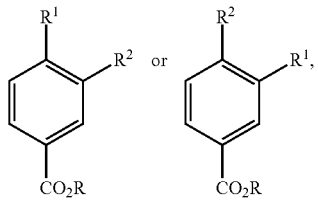

or a mixture thereof;

wherein R is H, alkyl, aryl, arylalkyl, cycloalkyl, or cycloalkylalkyl, and $R^1$ and $R^2$ are independently alkyl, alkoxyalkyl, arylalkyl, aryloxyalkyl, or arylalkoxyalkyl, or wherein $R^1$ and $R^2$ together with the atoms to which they are bonded form a cycloalkene ring of more than about six members; wherein any alkyl, alkoxyalkyl, arylalkyl, aryloxyalkyl, or arylalkoxyalkyl, or cycloalkene, of $R^1$ and $R^2$ can be substituted with alkyl, hydroxy, alkoxy, or carboxalkyl groups.

In various embodiments, the alkene of formula $R^1CH$=$CHR^2$ includes linear alkenes wherein the double bond is internal to the molecule. In various embodiments, the double bond is of the (E) configuration, e.g., in trans-4-octene.

In various embodiments, the invention provides a method of synthesis of a linker-bonded benzoate dimer of formula

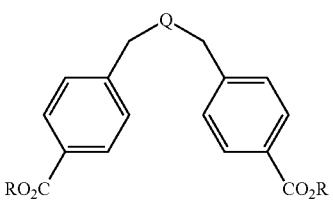

wherein both R groups are H, alkyl, aryl, arylalkyl, cycloalkyl, or cycloalkylalkyl, and Q is an alkylene group of at least one carbon; comprising contacting a coumalate compound of formula (I)

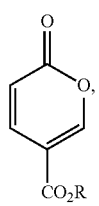

an alkene of formula $CH_2$=$CHCH_2QCH_2CH$=$CH_2$, a metal oxidation catalyst, and an oxidant, under conditions suitable to provide the substituted linker-bonded benzoate dimer.

EXAMPLES

All starting materials were commercially available unless otherwise noted. Methyl coumalate was prepared via methylation of coumalic acid[8]. Allyl heptyl ether was prepared from 1-heptanol and allyl bromide.[9]

Typical Reaction Procedure:

Methyl coumalate (200 mg), olefin (5 molar equivalents), and 50 mg Pd/C are dissolved in 7 mL mesitylene. The reaction is heated in a sealable tube in an oil bath at 200° C. overnight. The reaction vessel is then cooled to room temperature, where the catalyst is removed by filtering through a pad of Celite, and washing with ether. The filtrate is then concentrated and purified by silica gel column chromatography (10:1 hexanes/ethyl acetate).

Methyl 4-heptylbenzoate (4a)

$^1$H NMR (300 MHz, $CDCl_3$): ∂ 7.95 (d, J=7 Hz, 2H), 7.23 (d, J=7 Hz, 2H), 3.90 (s, 3H), 2.65 (m, 2H), 1.59-1.26 (m), 0.88; $^{13}$C NMR (400 MHz, $CDCl_3$): ∂ 167.4, 144.3, 129.9, 128.9, 127.3, 52.3, 32.1, 30.0, 29.2, 26.4, 22.9, 14.3; HRMS (FAB) m/z exact mass calculated for $C_{15}H_{22}$—$O_2$ 235.1693 ($MH^+$). found 235.1699.

Methyl 4-octylbenzoate (4b)

$^1$H NMR (300 MHz, $CDCl_3$): ∂ 7.94 (d, J=7 Hz, 2H), 7.24 (d, J=7 Hz, 2H), 3.90 (s, 3H), 2.63 (m, 2H), 1.59-1.26 (m), 0.88; $^{13}$C NMR (400 MHz, $CDCl_3$): ∂; 167.4, 148.7, 129.8, 128.6, 127.4, 52.1, 36.2, 32.1, 31.4, 29.8, 29.7, 29.5, 22.9, 14.3; HRMS (FAB) m/z exact mass calculated for $C_{16}H_{24}O_2$ 249.1849 ($MH^+$). found 249.1815.

Methyl 4-nonylbenzoate (4c)

$^1$H NMR (300 MHz, $CDCl_3$): ∂ 7.96 (d, J=7 Hz, 2H), 7.24 (d, J=7 Hz, 2H), 3.90 (s, 3H), 2.64 (m, 2H), 1.59-1.26 (m), 0.88; $^{13}$C NMR (400 MHz, $CDCl_3$): ∂ 167.5, 148.7, 129.8, 128.6, 127.4, 52.1, 36.3, 32.1, 31.4, 29.8, 29.7, 29.6, 29.5, 23.5, 14.4; HRMS (FAB) m/z exact mass calculated for $C_{17}H_{26}O_2$ ($MH^+$) 263.2006. found 263.2005.

Methyl 4-benzylbenzoate (4d)

Spectral data matches that of previous paper[7]

Methyl 4-(phenoxymethyl)benzoate (4e)

$^1$H NMR (300 MHz, $CDCl_3$): ∂ 8.05 (d, J=7 Hz, 2H), 7.51 (d, J=7 Hz, 2H), 7.31-6.91 (m, 5H), 5.13 (s, 2H), 3.92 (s, 3H); $^{13}$C NMR (400 MHz, $CDCl_3$): ∂ 167.1, 158.6, 142.5, 129.1, 128.9, 127.2, 121.4, 115.0, 69.5, 52.4; HRMS (FAB) m/z exact mass calculated for $C_{13}H_{14}O_3$ 243.1016 ($MH^+$). found 243.1009.

Methyl 4-(heptyloxymethyl)benzoate (4f)

$^1$H NMR (300 MHz, CDCl$_3$): ∂ 8.03 (d, J=7 Hz, 2H), 7.39 (d, J=7 Hz, 2H), 4.55 (s, 2H), 3.75 (m, 2H), 1.53-1.28 (m), 0.88; $^{13}$C NMR (400 MHz, CDCl$_3$): ∂ 167.2, 144.3, 130.3, 128.9, 127.8, 72.0, 70.7, 52.3, 32.1, 29.9, 29.4, 26.4, 22.9, 14.3; HRMS (FAB) m/z exact mass calculated for C$_{16}$H$_{24}$O$_3$ 265.1798 (MH$^+$). found 265.1804.

4-Pentylbenzoic acid (8a)

$^1$H NMR (400 MHz, CDCl$_3$): ∂ 12.06-11.6 (br, 1H), 8.05 (d, J=7 Hz, 2H), 7.29 (d, J=7 Hz, 2H) 2.70 (t, J=7 Hz, 2H), 1.73-1.53 (m, 2H) 1.53-1.22 (m, 4H), 0.93 (t, J=7 Hz, 3H); $^{13}$C NMR (100 MHz, CDCl3): ∂ 172.8, 65 149.8, 130.5, 128.8, 127.1, 36.3, 31.7, 31.1, 22.8, 14.3; HRMS (QTOF) m/z exact mass calculated for C$_{12}$H$_{16}$O$_2$ 192.115. found 191.1078 (M-H)-.

4-Octylbenzoic acid (8b)

$^1$H NMR (300 MHz, CDCl$_3$): ∂ 12.54-12.12 (br, 1H), 8.02 (d, J=7 Hz, 2H), 7.27 (d, J=7 Hz, 70 2H), 2.67 (t, J=7 Hz, 2H), 1.70-1.51 (m, 2H), 1.37-1.17 (m, 10H), 0.88 (t, J=7 Hz); $^{13}$C NMR (100 MHz, CDCl$_3$): ∂ 178.7, 149.8, 130.5, 128.8, 115.6, 36.4, 32.1, 31.4, 29.9, 29.7, 29.5, 22.9, 14.4; HRMS (QTOF) m/z exact mass calculated for C$_{15}$H$_{22}$O$_2$ 234.162, found 233.1547 (M-H)-. 75

4-Nonylbenzoic acid (8c)

$^1$H NMR (300 MHz, CDCl$_3$): ∂ 12.42-11.99 (br, 1H), 8.03 (d, J=7 Hz, 2H), 7.27 (d, J=7 Hz, 2H), 2.67 (t, J=7 Hz, 2H), 1.70-1.55 (m, 2H), 1.40-1.20 (m, 12H), 0.89 (t, J=7 Hz, 3H); $^{13}$C NMR (100 MHz, CDCl$_3$): ∂ 172.8, 149.8, 130.5, 128.8, 127.1, 36.4, 32.2, 31.4, 29.9, 29.7, 80 29.6, 29.5, 22.9, 14.4; HRMS (QTOF) m/z exact mass calculated for C$_{16}$H$_{24}$O$_2$ 248.1776. found 247.1704 (M-H)-.

4-Benzylbenzoic acid (8d)

$^1$H NMR (300 MHz, CDCl$_3$): ∂ 12.3-11.2 (br, 1H), 8.05 (d, J=7 Hz, 2H), 7.40-7.21 (m, 7H), 4.06 (s, 2H); $^{13}$C NMR (100 MHz, CDCl$_3$): ∂ 172.5, 147.8, 140.2, 85 129.2, 129.1, 128.8, 128.3, 127.5, 126.7, 42.3; HRMS (QTOF) m/z exact mass calculated for C$_{14}$H$_{12}$O$_2$ 212.0837. found 211.0765 (M-H)-.

4-(Phenoxymethyl)benzoic acid (8e)

$^1$H NMR (300 MHz, CDCl$_3$): ∂ 9.94 (br, 1H), 7.36-7.25 (m, 6H), 7.12-6.80 (m, 6H), 90 5.16 (s, 2H); $^{13}$C NMR (100 MHz, CDCl$_3$): ∂ 172.0, 152.6, 141.0, 130.5, 130.0, 129.7, 127.6, 121.1, 115.6, 69.3; HRMS (QTOF) m/z exact mass calculated for C$_{14}$H$_{12}$O$_3$ 228.0789. found 227.0714 (M-H)-.

4-(Heptyloxy)methyl)benzoic acid (8f)

$^1$H NMR (300 MHz, 95 CDCl$_3$): ∂9.93 (br, 1H), 8.05 (d, J=7 Hz, 2H), 7.43 (d, J=7 Hz, 2H), 4.56 (s, 2H), 3.63 (d, J=7 Hz, 2H), 1.64-1.15 (m, 10H), 0.87 (t, J=7 Hz, 3H); $^{13}$C NMR (100 MHz, CDCl$_3$): ∂ 171.9, 145.1, 128.8, 128.0, 127.5, 71.5, 71.1, 32.1, 29.9, 29.4, 26.5, 22.9, 14.3; HRMS (QTOF) m/z exact mass calculated for C$_{15}$H$_{22}$O$_3$ 250.1569. found 250.1576.

The reactions shown in Table 3 were carried out using substantially the same methodology as described above in the specific Examples.

Mono-Methyl Isophthalate (H)

To a solution of acrylic acid (0.206 mL, 3 mmol), distilled to remove polymerized material, in toluene (5 mL, 0.2 M) was added N,N-diisopropylethylamine (0.174 mL, 1 mmol) dropwise at rt. The mixture was stirred for 30 min after which methyl coumalate (0.152 g, 1 mmol) was added, followed by 10% Pd/C (0.038 g, 25%/mass). The reaction was heated to 140° C. for 15 h, then cooled and quenched with sat. aq. NH$_4$Cl solution (10 mL). The aqueous layer was extracted with EtOAc and the combined organic extracts were washed with brine and dried over MgSO$_4$. Filtration and concentration in vacuo gave the crude product which was purified via flash column chromatography (5:1-3:1 hexanes:EtOAc) to give mono-methyl isophthalate in 45% yield as a light yellow solid.

DOCUMENTS CITED

1. G. A. Kraus "Synthetic Methods for the Preparation of 1,3-Propanediol" *Clean Soil, Air, Water,* 2008, 36, 648-651.
2. Gong, W. H. (BP Corporation North America Inc., USA). Production of terephthalic acid from 2,5-furandicarboxylate. PCT Int. Appl. (2009), 19 pp.; Chemical Indexing Equivalent to 149:10481 (US). CODEN: PIXXD2 WO 2009064515 A1 20090522 Application: WO 2008-US63703 20080515. Priority: US2007-940097 20071114. CAN 150:540266.
3. Afarinkia, K.; Vinader, V.; Nelson, T. D.; Posner, G. H. *Tetrahedron,* 1992, 48, 9111-9171.
4. Bryson, T. A.; Donelson, D. M. *J. Org. Chem.,* 1977, 42, 2930-2931.
5. P. M. Delaney, D. L. Browne, H. Adams, A. Plant, J. P Harrity, *Tetrahedron,* 2007, 64, 866-873.
6. Matsushita, Y.; Sakamoto, K.; Murakami, T.; Matsui, T. *Synth. Commun.* 1994, 24, 3307-3313.
7. Amatorea, M.; Gosmin, C.; *Chem. Comm.* 2008, 40, 5019-21.
8. Ashworth, I. W.; Bowden, M. C.; Dembofsky, B.; Levin, D.; Moss, W.; Robinson, E.;
9. R. Fellous, J. P. Rabine, L. Lizzani-Cuvelier, R. Luft, *Bull. Soc. Chim. France* 1974, (5-6, Pt. 2), 923-924.
10. R. J. Sheehan, "Terephthalic Acid, Dimethyl Terephthalate and Isophthalic Acid" in *Ullman's Encyclopedia of Industrial Chemistry,* Wiley-VCH, Weinheim (2005).

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of synthesis of a para-substituted benzoate, comprising contacting a coumalate compound of formula (I)

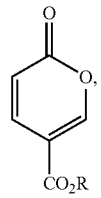
(I)

an alkene of formula $CH_2$=$CHR^1$, a metal oxidation catalyst, and an oxidant, under conditions suitable to provide the para-substituted benzoate of formula

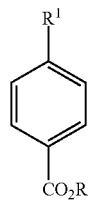

wherein R is H, alkyl, aryl, arylalkyl, cycloalkyl, or cycloalkylalkyl, and
$R^1$ is alkyl, alkoxyalkyl, arylalkyl, aryloxyalkyl, or arylalkoxyalkyl.

2. The method of claim 1 wherein R is methyl or hydrogen.

3. The method of claim 1 wherein the metal oxidation catalyst comprises palladium.

4. The method of claim 1 wherein the oxidant is oxygen or ambient air.

5. The method of claim 1 wherein the conditions comprise contacting the coumalate compound of formula (I) and the alkene at an elevated temperature, optionally in a solvent.

6. The method of claim 5 wherein the solvent comprises a hydrocarbon, an ether, or both, having a boiling point of not less than about 190° C.

7. The method of claim 1 wherein R is alkyl, aryl, arylalkyl, cycloalkyl, or cycloalkylalkyl and the para-substituted benzoate is provided in at least about 50% yield.

8. The method of claim 1 further comprising conversion of the para-substituted benzoate to a terephthalate by oxidation of group $R^1$ wherein the terephthalate is substantially free of an isophthalate.

9. A method of synthesis of a disubstituted benzoate, comprising contacting a coumalate compound of formula (I)

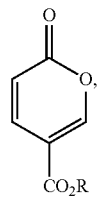
(I)

an alkene of formula $R^1CH$=$CHR^2$, a metal oxidation catalyst, and an oxidant, under conditions suitable to provide the substituted benzoate of formula

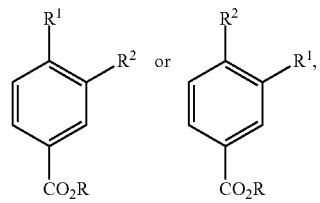

or a mixture thereof;
wherein R is H, alkyl, aryl, arylalkyl, cycloalkyl, or cycloalkylalkyl, and
$R^1$ and $R^2$ are independently alkyl, alkoxyalkyl, arylalkyl, aryloxyalkyl, or arylalkoxyalkyl, or,
$R^1$ and $R^2$ together with the atoms to which they are bonded form a cycloalkene ring of more than about six members; wherein any alkyl, alkoxyalkyl, arylalkyl, aryloxyalkyl, or arylalkoxyalkyl, or cycloalkene, of $R^1$ and $R^2$ can be substituted with alkyl, hydroxy, alkoxy, or carboxyalkyl groups.

10. The method of claim 9 wherein R is methyl or hydrogen.

11. The method of claim 9 wherein the metal oxidation catalyst comprises palladium.

12. The method of claim 9 wherein the oxidant is oxygen or ambient air.

13. The method of claim 9 wherein the conditions comprise contacting the coumalate compound of formula (I) and the alkene at an elevated temperature, optionally in a solvent.

14. The method of claim 13 wherein the solvent comprises a hydrocarbon, an ether, or both, having a boiling point of not less than about 190° C.

15. A method of synthesis of a linker-bonded benzoate dimer of formula:

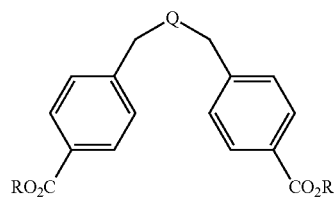

wherein both R groups are H, alkyl, aryl, arylalkyl, cycloalkyl, or cycloalkylalkyl, and,
Q is an alkylene group of at least one carbon atom;
comprising contacting a coumalate compound of formula (I)

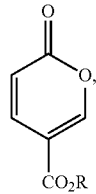
(I)

an alkene of formula $CH_2$=$CHCH_2QCH_2CH$=$CH_2$, a metal oxidation catalyst, and an oxidant, under conditions suitable to provide the substituted linker-bonded benzoate dimer.

16. The method of claim 15 wherein R is H or alkyl.

17. The method of claim 15 wherein the metal oxidation catalyst comprises palladium.

18. The method of claim 15 wherein the oxidant is oxygen or ambient air.

19. The method of claim 15 wherein the conditions comprise contacting the coumalate compound of formula (I) and the alkene at an elevated temperature, optionally in a solvent.

20. The method of claim 19 wherein the solvent comprises a hydrocarbon, an ether, or both, having a boiling point of not less than about 190° C.

* * * * *

UNITED STATES PATENT AND TRADEMARK OFFICE
CERTIFICATE OF CORRECTION

PATENT NO. : 9,000,209 B2
APPLICATION NO. : 14/234079
DATED : April 7, 2015
INVENTOR(S) : George A. Kraus It is certified that error appears in the above-identified patent and that said Letters Patent is hereby corrected as shown below:

Title page, item (56) "Other Publications", line 8, delete "Palladiumb" and insert --Palladium--, therefor Specification In column 3, line 1, delete "$CH^2$=$CHR^1$" and insert --$CH_2$=$CHR^1$--, therefor In column 3, line 26, delete "telephthalate" and insert --terephthalate--, therefor In column 4, line 64, delete "125-175° C." and insert --125-175°C.--, therefor In column 5, Scheme 2, (a) line 2, delete "140° C." and insert --140°C.--, therefor In column 6, line 33, after "from", insert --1--, therefor In column 9, line 33, delete "140° C." and insert --140°C.--, therefor In column 9, Table 2, entry 1, delete "-$(CH_2)_6$CH3" and insert -- -$(CH_2)_6CH_3$--, therefor In column 9, Table 2, entry 2, delete "-$(CH_2)_7$CH3" and insert -- -$(CH_2)_7CH_3$--, therefor In column 9, Table 2, entry 3, delete "-$(CH_2)_8$CH3" and insert -- -$(CH_2)_8CH_3$--, therefor In column 9, Table 2, entry 6, delete "-$CH_2O(CH_2)_6$CH3" and insert -- -$CH_2O(CH_2)_6CH_3$--, therefor In column 10, line 41, delete "CO," and insert --$CO_2$--, therefor In column 10, line 62-63, delete "140° C. to 200° C." and insert --140°C. to 200°C.--, therefor Signed and Sealed this
First Day of December, 2015

Michelle K. Lee
*Director of the United States Patent and Trademark Office*

CERTIFICATE OF CORRECTION (continued)
U.S. Pat. No. 9,000,209 B2

Specification

In column 10, line 66, delete "190° C." and insert --190°C.--, therefor

In column 11, line 4, delete "140° C." and insert --140°C.--, therefor

In column 14, line 16, delete "200° C." and insert --200 °C.--, therefor

In column 14, line 31, delete "($MH^+$)." and insert --($MH^+$),--, therefor

In column 14, line 42, delete "($MH^+$)." and insert --($MH^+$),--, therefor

In column 14, line 52, delete "263.2006." and insert --263.2006,--, therefor

In column 14, line 66, delete "$C_{13}H_{14}O_3$" and insert --$C_{15}H_{14}O_3$--, therefor In column 14, line 66, delete "($MH^+$)." and insert --($MH^+$),--, therefor In column 15, line 8, delete "($MH^+$)." and insert --($MH^+$),--, therefor In column 15, line 18, delete "192.115." and insert --192.115,--, therefor In column 15, line 38, delete "248.1776." and insert --248.1776,--, therefor In column 15, line 46, delete "212.0837." and insert --212.0837,--, therefor In column 15, line 54, delete "228.0789." and insert --228.0789,--, therefor In column 15, line 63, delete "250.1569." and insert --250.1569,--, therefor In column 16, line 1, delete "(H)" and insert --(II)--, therefor In column 16, line 8, delete "140° C." and insert --140°C.--, therefor In column 16, line 48, delete "Ullman's" and insert --Ullmann's--, therefor

Claims

In column 17, line 43, in Claim 6, delete "190° C." and insert --190°C.--, therefor In column 18, line 34, in Claim 14, delete "190° C." and insert --190°C.--, therefor In column 19, line 11, in Claim 20, delete "190° C." and insert --190°C.--, therefor